United States Patent [19]
Chapoteau et al.

[11] Patent Number: 5,891,736
[45] Date of Patent: Apr. 6, 1999

[54] REAGENTS AND METHODS FOR RELEASING AND MEASURING LEAD IONS FROM BIOLOGICAL MATRICES

[75] Inventors: Eddy Chapoteau, Brooklyn; Bronislaw P. Czech, Peekskill; Jonathan Craine, Monsey, all of N.Y.

[73] Assignee: Bayer Corporation, Tarrytown, N.Y.

[21] Appl. No.: 752,869

[22] Filed: Nov. 20, 1996

Related U.S. Application Data

[60] Provisional application No. 60/020,036 Jun. 21, 1996.
[51] Int. Cl.$^6$ .............................. G01N 33/20; G01N 1/18
[52] U.S. Cl. .............................. 436/74; 436/73; 436/177; 436/178
[58] Field of Search ................................ 436/74, 73, 177, 436/178

[56] References Cited

U.S. PATENT DOCUMENTS 5,407,831   4/1995   Jing ............................................. 436/74
5,631,139   5/1997   Wong et al. ............................... 435/18

*Primary Examiner*—Stephen Walsh
*Assistant Examiner*—Daryl A. Basham
*Attorney, Agent, or Firm*—Andrew L. Klawitter; Rodman & Rodman

[57] ABSTRACT

The present invention provides a reagent for extracting lead ions from a variety of biological matrices such as human whole blood that has been anticoagulated with either heparin or EDTA, and lyophilized human blood and bovine EDTA whole blood. The released lead is measured in situ with a colorimetric porphyrin reagent without further manipulation of the supernatant. The lead ion releasing reagent can be used in conjunction with a variety of assay formats for the determination of lead in various biological fluids.

71 Claims, 3 Drawing Sheets

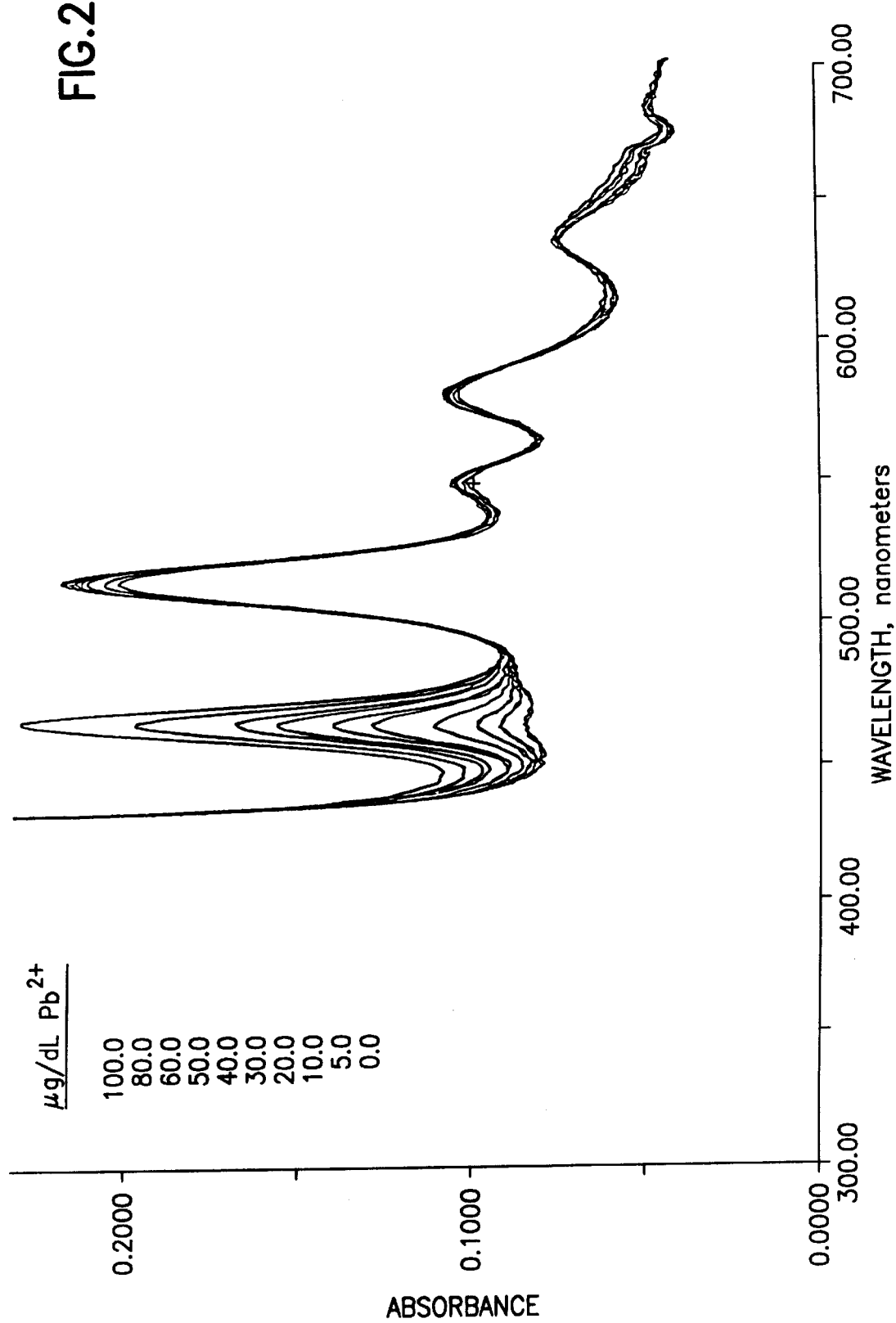

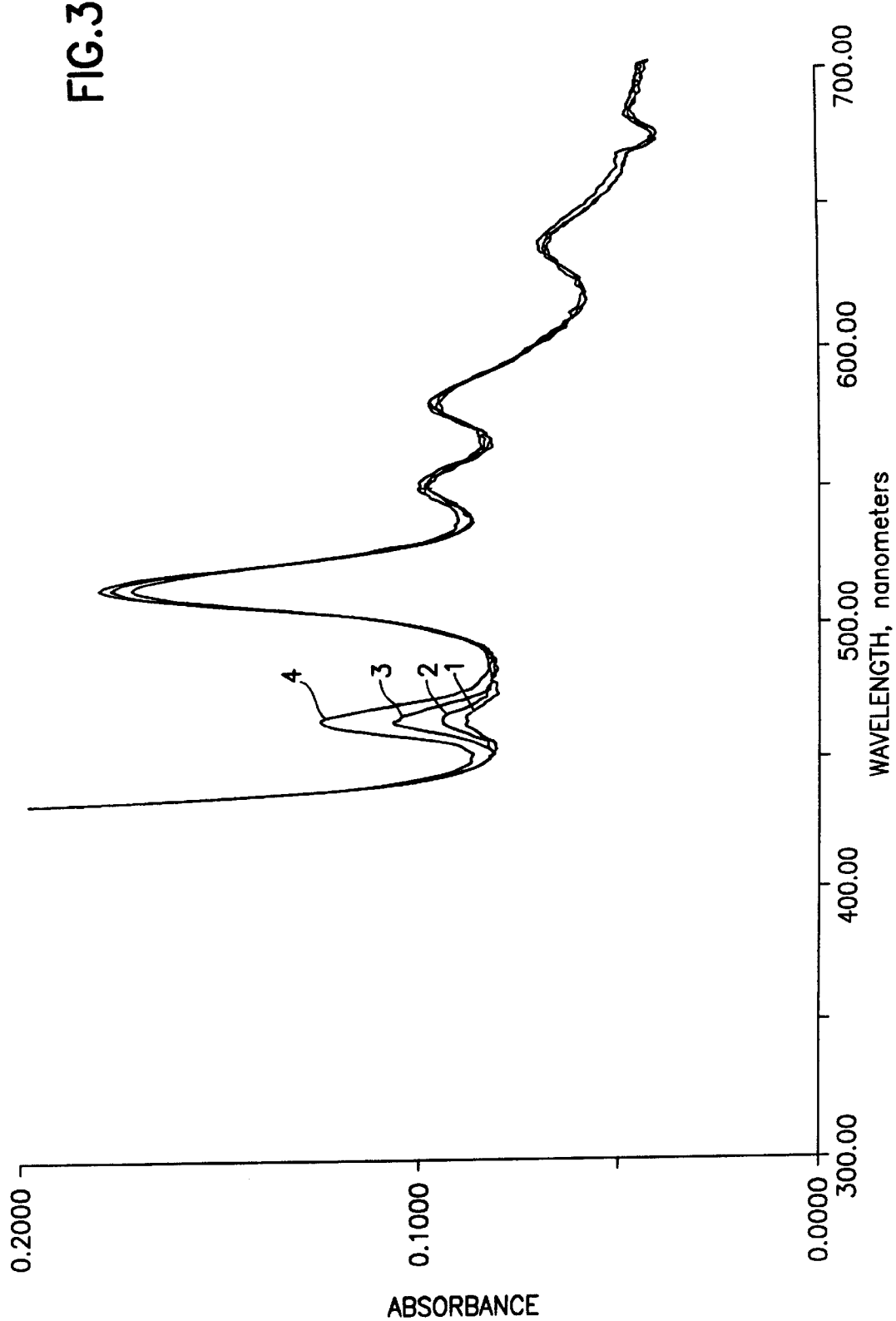

REAGENTS AND METHODS FOR RELEASING AND MEASURING LEAD IONS FROM BIOLOGICAL MATRICES

This application claims the benefit of U.S. Provisional Application Ser. No. 60/020,036 filed Jun. 21, 1996.

BACKGROUND OF THE INVENTION

1. Field of the Invention

The present invention relates to reagents and methods for releasing and measuring lead in blood.

2. Background Discussion

Lead and its compounds have become widely distributed in the environment over the centuries. Lead is known to be toxic and have deleterious effects on humans. The toxicity of lead is well documented. Trace amounts of lead can adversely affect the function of various organs of the human body, especially in small children. It is now generally recognized that lead poisoning occurs at blood levels as low as 10 to 15 $\mu$g/dL. Thus, the detection and measurement of lead in blood is extremely important in providing universal blood screening and in monitoring occupational lead exposure.

Most lead screening programs use atomic absorption or anodic stripping voltametry methods for the determination of trace amounts of lead. Both methods are cumbersome to use, susceptible to contamination, and costly. Enzyme-based biodetection systems of lead, which employ δ-aminolevulinic acid dehydrase (ALAD) and isocitrate dehydrogenase, have also been proposed. An automated fluorimetric lead assay, which uses inhibition of ALAD by lead is disclosed in PTC International Publication No. WO95/17679 to Wong et al., which discloses the detection of lead in a sample by adding a lead recovery agent to an assay solution containing lead, adding a disulfide enzyme to the assay solution and correlating the activity of the disulfide enzyme to the amount of lead in the sample.

The Wong et al. patent discloses the use of acids such as trichloroacetic acid, nitric acid, 5-sulfosalicylic acid, or perchloric acid as an initial treatment step in separating lead ions from a blood sample. However, the resulting lead-containing aqueous supernatant must be neutralized with a buffer containing a lead recovery agent before analysis. Otherwise, the lead is unavailable for measurement.

Other methods of sample pretreatment include acid digestion or dilution of blood with a matrix modifier such as a nitric acid solution of ammonium phosphate and a nonionic surfactant, prior to analysis by atomic absorption.

SUMMARY OF THE INVENTION

The present invention relates to the release and measurement of the lead content of a biological matrix such as whole blood, with anticoagulants such as heparin or ethylenediamine tetraacetic acid (EDTA). A releasing reagent is used to extract the lead content in the form of lead ions from the biological matrix into a supernatant liquid, and comprises an acid solution capable of releasing lead ions from the biological matrix, and at least one or more salts capable of solubilizing the released lead ions from the biological matrix.

When EDTA is used as the anticoagulant, an EDTA complexing ion is used to block the released lead ions from complexing with EDTA and thereby prevent complexation of the released lead ions by EDTA.

The invention also relates to a colorimetric reagent that is used to determine the amount of released lead ions, comprising porphyrin and a quaternary ammonium salt.

BRIEF DESCRIPTION OF THE DRAWINGS

In the accompanying drawings,

FIG. 2 is a spectral response curve for the determination of lead.

FIG. 3 is another spectral response curve for the determination of lead.

DESCRIPTION OF THE PREFERRED EMBODIMENTS

Figure 1:
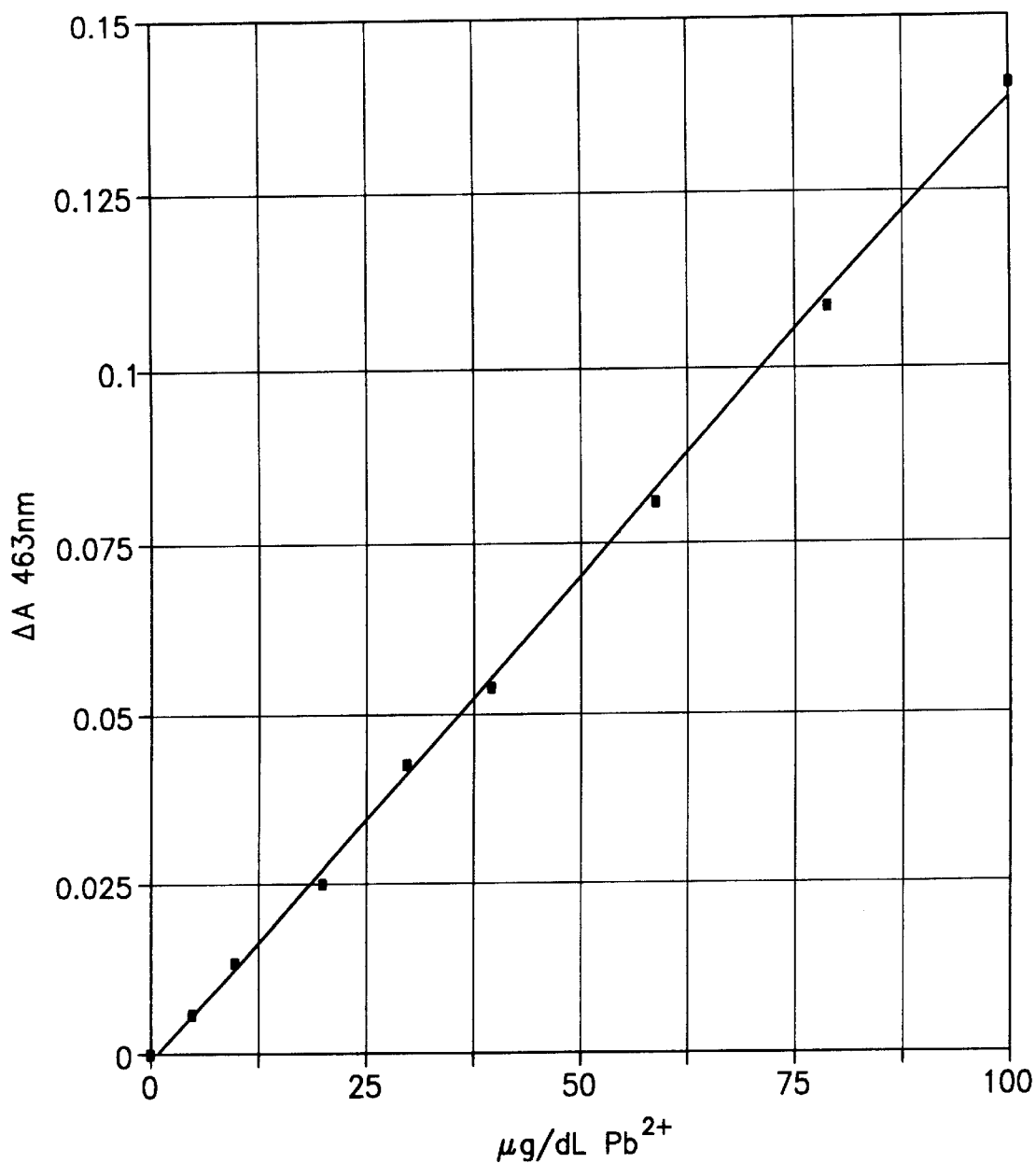
FIG. 1 is an absorbance response curve for the determination of lead.

The present invention provides a novel reagent for the extraction of lead ions from a biological matrix such as human or bovine whole blood, or lyophilized human whole blood. The matrices can also be anticoagulated with either heparin or EDTA. The invention also provides a means for measuring released lead ions in a concentration range of above 0 to about 100 $\mu$g/dL $Pb^{2+}$.

As used herein, the terms "release", "extraction" and "recovery" of lead from the biological matrix denote that substantially all of the lead ions present in the original biological matrix after treatment with the acidic reagent of the present invention can be found in the supernatant liquid that contains the extracted lead ions. The terms "lead" and lead content" as used herein refer to the lead ion content, and are used in abbreviated form for convenience. Also as used herein, the term "whole blood" refers to blood that has been anticoagulated with an anticoagulant such as heparin or EDTA.

More specifically, about 90 to 110% and preferably 100% of the lead content in the original untreated biological matrix is present in the supernatant. Greater than 100% lead recoveries become possible due to lead contaminants that may be present in the reagents or in the analytical environment.

In accordance with the present invention, and with specific application to release and measurement of the lead ion content of whole blood, sufficient amounts of an acid capable of freeing or releasing lead ions from red blood cells are used in conjunction with sufficient amounts of at least one or more salts capable of solubilizing the released lead ions from the blood. This acid composition is also referred to as a "releasing reagent."

Suitable acids capable of freeing or releasing lead ions from red blood cells include trichloroacetic acid, perchloric acid, 5-sulfosalicylic acid, and other equivalent acids. A particularly preferred acid is ultrapure trichloroacetic acid, available for example from Fluka AG, Switzerland.

The salts capable of solubilizing the released lead ions from whole blood include those salts which have an alkali metal cation, such as sodium, potassium or lithium. The anionic portion of the salt can be a nitrate, chloride, bromide, and the like.

Preferred salts include the nitrates of sodium, potassium and lithium, with sodium nitrate being especially preferred.

When EDTA is used as the anticoagulant, sufficient amounts of an EDTA complexing ion are used to block the released lead ions from complexing with EDTA and thereby prevent complexation of the released lead ions by EDTA.

The salts capable of providing ions which can complex with EDTA to prevent complexation of lead ions by EDTA include those salts which have an alkaline earth metal cation, such as calcium, barium, magnesium, and strontium. The anionic portion of the salt can be a nitrate, chloride, bromide, and the like. Preferred salts include the nitrates of calcium, barium, magnesium and strontium, with calcium nitrate being especially preferred.

A trichloroacetic acid solution with high concentrations of sodium nitrate and calcium nitrate is used as the preferable universal reagent for freeing or releasing lead ions from whole blood that has been anticoagulated with either heparin or EDTA.

It has been found that a negligible amount of lead ions are released from whole blood by using only the trichloroacetic acid solution, without the lead ion solubilizing salts and the EDTA complexing salts.

More specifically, the releasing reagent includes about 5 to 25% (w/v), preferably about 8 to 15% (w/v), and most preferably about 10% (w/v) trichloroacetic acid. Amounts of trichloroacetic acid greater than 25% (w/v) can be used, however, such greater amounts have not been found to increase the effectiveness of the releasing reagent.

The concentration of lead ion solubilizing salts in the trichloroacetic acid solution can vary from about 0.2 to 1.0M, preferably about 0.3 to 0.8M, and most preferably about 0.5M.

The concentration of EDTA complexing salts in the trichloroacetic acid solution can vary from about 0.04 to 1M, preferably about 0.05 to 0.5M and most preferably about 0.08 to 0.3 with a concentration of 0.1M being particularly preferred.

It has been found that when the releasing reagent comprising the trichloroacetic acid solution containing sodium nitrate and calcium nitrate is contacted with whole blood, substantially all of the whole blood proteins are precipitated and substantially all of the lead ion content in the blood is quantitatively released and extracted in the form of a solution of the soluble lead ions in the supernatant liquid. The separation of the supernatant solution from the precipitate can be conveniently accomplished by centrifugation, filtration, and the like.

The sodium nitrate has been found to increase the efficiency and effectiveness of the trichloroacetic acid in precipitating blood proteins from whole blood, and in extracting the lead ions from the whole blood into the supernatant solution in the form of soluble lead nitrate.

The calcium ions in the calcium nitrate serve to mask or block the binding sites of the EDTA, and thereby prevent the EDTA from binding or complexing with lead ions. When used with non-EDTA anticoagulated whole blood, no adverse effects have been found to occur with the calcium nitrate present. Therefore, the trichloroacetic acid/sodium nitrate/calcium nitrate composition has been found to be an excellent releasing reagent for whole blood that has been anticoagulated with heparin or EDTA, or where the nature of the anticoagulant is unknown.

The whole blood mixture with the releasing reagent can then be centrifuged to separate the precipitated whole blood proteins from the supernatant liquid containing the soluble lead ions and other blood analytes. The lead ion content in the supernatant liquid can be measured with any suitable analytical method or device, such as atomic absorption, anodic stripping voltametry, spectrophotometry, enzyme based biodetection systems, and the like.

When using a spectrophotometric analyzer, the released lead ions in the supernatant liquid can be easily measured with a colorimetric porphyrin based reagent, in situ, without further manipulation of the supernatant. The method of measurement is based upon the spectral shift of the wavelength maximum of the free tetrakis (trimethylammoniophenyl)porphyrin in the colorimetric reagent, from 410 nanometers, which is an indication that no lead is present, to 463 nanometers, which is an indication that the colorimetric porphyrin reagent has become fully complexed with lead.

Other porphyrin compounds can also be used, such as tetrakis(1-methyl-4-pyridyl)porphyrin or tetrakis(trimethyl-ammoniobenzyl)porphyrin. The change in absorbance is proportional to the concentration of lead in the sample. It has been discovered that the addition of a soluble quaternary ammonium salt to the colorimetric porphyrin reagent increased the sensitivity of the colorimetric porphyrin reagent and improved the spectral response more than one order of magnitude. The addition of more than a sufficient amount of ammonium hydroxide has been found to mask interfering cations, such as copper and zinc and produces a highly alkaline medium to the colorimetric reagent.

The quaternary ammonium salts have the general structure:

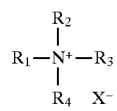

wherein $R_1$, $R_2$, $R_3$ and $R_4$ can be $C_1$ to $C_{18}$ alkyl; or wherein either $R_1$ or $R_2$ or $R_3$ or $R_4$ can be aralkyl, such as benzyl, and wherein X can be Cl, Br, I. Suitable quaternary ammonium salts include cetyltrimethylammonium bromide, benzalkonium chloride, octyldodecyldimethylammonium chloride, tetrapentylammonium bromide, and tetradecyltrimethylammonium bromide.

Polymeric quaternary ammonium salts of the following general structure are more preferable, and have the following general structure:

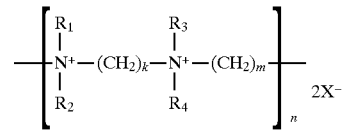

wherein $R_1$, $R_2$, $R_3$, $R_4$, can be $C_1$ to $C_4$ alkyl; k,m=2 to 10; X=Cl, Br, I and n=1–30. Especially preferred is hexadimethrine bromide.

The colorimetric porphyrin reagent is contacted in situ with the supernatant liquid containing the released lead ions and the residual releasing reagent without any special pretreatment. The concentration of the porphyrin compound in the colorimetric reagent can vary from about $5.0 \times 10^{-6}$ to $2.0 \times 10^{-5}$M, and preferably from about $2.5 \times 10^{-6}$ to $1 \times 10^{-5}$M. The ammonium hydroxide concentration in the colorimetric reagent can vary from about 0.2 to 2.0M, and preferably about 0.5 to 1.0M. The concentration of the quaternary ammonium salt can vary from about 0.002 to 0.1% (w/v) and preferably about 0.0025 to 0.005% (w/v) of the colorimetric reagent.

EXAMPLE 1

Preparation of Colorimetric Porphyrin Reagent for Lead Determination a) A 10-mL stock solution of 1.0 mM (millimolar) tetrakis (trimethylammoniophenyl)porphyrin in distilled water was prepared. An aliquot of 0.2 mL (milliliters) of this solution was added to 20 mL of 1.0M $NH_4OH$ and the resultant solution was stirred.

b) To the same solution prepared in a) was added 20 mg (milligrams) of hexadimethrine bromide (0.01% w/v), available under the trademark "Polybrene" from Sigma Chemical Company, and the mixture was stirred until the hexadimethrine bromide dissolved, to thereby form the colorimetric porphyrin reagent.

EXAMPLE 2

Preparation of Lead-Releasing Reagents a) 10.0 g (grams) of trichloroacetic acid were dissolved in 80 mL of water in a 100-mL volumetric flask and brought to the 100 mL volume with distilled, deionized water.

b) 10.0 g of trichloroacetic acid were dissolved in 80 mL of water in a 100 mL volumetric flask. 4.3 g of $NaNO_3$ were added, and the contents were brought to the 100-mL volume with distilled, deionized water, to form a 0.5M $NaNO_3$ solution with trichloroacetic acid.

c) 4.3 g $NaNO_3$ were dissolved in a solution of 10 g of trichloroacetic acid in deionized water. 1.64 g $Ca(NO_3)_2$ was added to the solution and the mixture was stirred until all solids dissolved. The solution was transferred to a 100-mL volumetric flask and brought to the 100 mL volume with distilled, deionized water, to form a solution of trichloroacetic acid with 0.5M $NaNO_3$ and 0.1M $Ca(NO_3)_2$.

EXAMPLE 3

Preparation of Lead-Spiked Whole Blood 2.0 mL blood samples were collected from human subjects in both heparin and EDTA tubes supplied by Becton Dickinson, Rutherford, N.J. To each of the heparin and EDTA tubes were added aliquots of 20 $\mu$g/mL lead stock solution in 1.0 mM $HNO_3$ made from a 1000 $\mu$g/dL atomic absorption lead standard from Aldrich Co., Milwaukee, Wis. Final solution concentrations of 10 to 100 $\mu$g/dL $Pb^{2+}$ in 10 $\mu$g increments were prepared. Thereafter, each test tube was vortexed on a vortex mixer (Fisher Scientific Industries) for one minute and placed on a rotary mixer (Fisher Scientific Industries) for ½ hour to obtain a homogeneous solution.

EXAMPLE 4

Pretreatment of Whole Blood with Releasing Reagent 0.3 mL amounts of whole blood from each test tube from Example 3 were pipetted into separate 1-mL centrifuge tubes. 0.3 mL of one lead releasing reagent selected from Example 2a, 2b or 2c was added to each tube. The resultant mixture in each tube was vortexed for one minute, followed by centrifugation at 14,000 rpm (revolutions per minute) on a centrifuge (Eppendorf Model 5415C). The resultant supernatant (0.4 mL) from each centrifugation was decanted into a dry test tube, prerinsed with deionized water. Subsequent treatment is detailed in the examples which follow.

EXAMPLE 5

Preparation of Aqueous Lead Standards

A 100 $\mu$g/dl $Pb^{2+}$ solution was prepared by pipetting 0.1 mL of a 1000 $\mu$g/mL atomic absorption lead standard into a 100-mL volumetric flask. The flask was filled to volume with a solution of 5% trichloroacetic acid, 0.25M $NaNO_3$, and 0.05M $Ca(NO_3)_2$. Aliquots (0.5, 1.0, 2.0, 3.0, 4.0, 5.0, 6.0, 8.0, 10.0 mL) of the 100 $\mu$g/dl $Pb^{2+}$ solution were pipetted into 10 mL volumetric flasks and filled to volume with a solution of 5% trichloroacetic acid, 0.25M $NaNO_3$, and 0.05M $Ca(NO_3)_2$ to make 5, 10, 20, 30, 40, 50, 60, 80, 100 $\mu$g/dl $Pb^{2+}$ standards, respectively.

EXAMPLE 6

Determination of Lead with the Porphyrin Reagent

A. Standard Curve 1 mL of the calorimetric porphyrin reagent from Example 1 b) was pipetted into a number of 1.5-mL cuvettes (path length, 1=1 cm). To each cuvette was added 0.2 mL of one of the aqueous lead standard concentrations from Example 5. The mixture thereby formed was stirred to form a homogeneous solution and allowed to stand at room temperature for 10 minutes. The absorbance at 463 nm versus reagent without lead added (reagent blank) was read on a Cary-3 spectrophotometer (Varian Analytical Instruments). Absorbance data at 463 nm is tabulated in Table 1 and was plotted versus $\mu$g/dL $Pb^{2+}$ to obtain the response curve in FIG. 1. FIG. 2 shows the spectral response.

TABLE 1

ABSORBANCE READINGS FOR THE PORPHYRIN REAGENT WITH LEAD STANDARDS

| $\mu$g/dL $Pb^{2+}$ | $\Delta A_{463}$ nm |
|---|---|
| 0.0 | 0.0000 |
| 5.0 | 0.0060 |
| 10.0 | 0.0136 |
| 20.0 | 0.0247 |
| 30.0 | 0.0421 |
| 40.0 | 0.0532 |
| 50.0 | 0.0690 |
| 60.0 | 0.0804 |
| 80.0 | 0.1081 |
| 100.0 | 0.1408 |

FIG. 1 shows the linearity of the lead response of the calorimetric porphyrin reagent, and that lead ions can be measured over a wide concentration range (0–100 $\mu$g/dL) with the colorimaetric porphyrin reagent.

The response of the porphyrin reagent to interfering cations, such as copper and zinc was also assessed. No change in $A_{463}$ nm (absorbance at 463 nanometers) was observed in the presence of 150 $\mu$g/dl $Zn^{2+}$ or a mixture of 100 $\mu$g/dl $Cu^{2+}$ and 100 $\mu$g/dl $Zn^{2+}$. The potential interference from these cations was eliminated by the use of ammonium hydroxide as a mask in Example 1.

B. Procedure for Analysis of Supernatant Obtained From the Pretreatment of Whole Blood with Releasing Agent 1.0 mL of the colorimetric porphyrin reagent from Example 1 was pipetted into a 1.5 mL centrifuge tube. The supernatant liquid (0.2 mL) from the pretreatment of whole blood in Example 4 with selected releasing reagents from Examples 2a, 2b and 2c was added to form an assay mixture. Each mixture was mixed and centrifuged for 10 minutes at 14,000 rpm in an Eppendorf Model 5415C centrifuge. An aliquot (1.0 mL) was transferred into a 1.5 mL cuvette (1=1 cm) and the absorbance at 463 nm was read on a Cary 3 spectrophotometer.

EXAMPLE 7

Analysis of Heparinated Whole Blood

A. This example details the analysis of heparinated whole blood from Example 3 pretreated according to the procedure of Example 4 with 10% (w/v) trichloroacetic acid prepared in Example 2a.

The supernatants were assayed according to the procedure of Example 6B with the colorimetric porphyrin reagent containing 0.01% w/v hexadimethrine bromide (Example 1b) or without hexadimethrine bromide (Example 1a). No absorbance change of the colorimetric porphyrin reagent was observed in the presence of the supernatants, which indicates that no detectable amount of lead was released in the supernatants of whole blood samples to which up to 100 µg/dL $Pb^{2+}$ was added.

B. This example details the analysis of heparinated whole blood pretreated according to the procedure of Example 4 with 10% (w/v) trichloroacetic acid and 0.5M $NaNO_3$ prepared as in Example 2b. Table 2 shows data for the supernatants analyzed with the colorimetric porphyrin reagent of Example 1 according to the procedure of Example 6B.

TABLE 2

| | $\Delta A_{463\ nm}$ | |
|---|---|---|
| µg/dL $Pb^{2+}$ | Column A | Column B |
| 0.0 | 0.0000 | 0.0000 |
| 100.0 | 0.0027 | 0.0370 |
| % (w/v) hexadimethrine bromide | 0.00 | 0.01 |

The increase in $\Delta A_{463}$, in Table 2, column A, shows that the addition of $NaNO_3$ to the trichloroacetic acid promoted the release of lead ions. Data in Table 2, column B shows that the addition of hexadimethrine bromide to the porphyrin reagent increased sensitivity. The hexadimethrine bromide, a heparin antagonist, liberated the lead ions in the supernatant from its weak interaction with the residual heparin and improved the spectral response by more than one order of magnitude.

The data in Table 3 shows absorbance readings of the heparinated whole blood with different concentrations of lead ions when the supernatant was analyzed with the colorimetric porphyrin reagent containing 0.01% w/v hexadimethrine bromide according to the procedure of Example 6B. A Cary-3 spectrophotometer was used to record the data.

TABLE 3

| Heparinated Whole Blood | |
|---|---|
| µg/dL $Pb^{2+}$ | $\Delta A_{463\ nm}$ |
| 0.0 | 0.0000 |
| 10.0 | 0.0066 |
| 20.0 | 0.0144 |
| 30.0 | 0.0190 |
| 40.0 | 0.0230 |

The data in Table 4 represents changes in absorbance readings ($\Delta A_{463\ nm}$) of the colorimetric porphyrin reagent in contact with 20 and 40 µg/dL $Pb^{2+}$ lead standards from Example 5, diluted 1:1 with the releasing agent from Example 2b according to Example 6A.

TABLE 5

Recoveries of Lead Added to Heparinated Whole Blood

| µg/dL $Pb^{2+}$ | |
|---|---|
| added | found |
| 0.0 | 0.0 |
| 10.0 | 10.8 |
| 20.0 | 23.6 |
| 30.0 | 31.1 |
| 40.0 | 37.7 |

The recovery data in Table 5 were calculated using the absorbance information from the standards shown in Table 4 and the absorbances of the heparinated whole blood shown in Table 3, in accordance with the following equation:

$$\mu g/dL\ Pb^{2+}(found) = A_{463}(sample)/A_{463}(std) \times \mu g/dL\ Pb^{2+}(std) \quad [I]$$

TABLE 4

| STD (µg/dL $Pb^{2+}$) | $\Delta A_{463\ nm}$ |
|---|---|
| 0.0 | 0.0000 |
| 20.0 | 0.0122 |
| 40.0 | 0.0210 |

The above results indicate that the addition of 0.5M $NaNO_3$ to the 10% trichloroacetic acid promoted the quantitative release of lead ions added to heparinated whole blood, in contrast to a negligible amount of lead ions released when only trichloroacetic acid was used.

EXAMPLE 8

Analysis of EDTA Treated Whole Blood

A. This example details the analysis of EDTA treated whole blood pretreated according to the procedure of Example 4 with 10% (w/v) trichloroacetic acid and 0.5M $NaNO_3$ from Example 2b. The absorbance data in Table 6 was obtained in accordance with the procedure of Example 6B.

The results shown in Table 6 indicate that the 10% (w/v) trichloroacetic acid and 0.5M $NaNO_3$ releasing reagent cannot extract lead ions quantatively from whole blood anticoagulated with EDTA. The majority of lead ions were unavailable for complexation with the colorimetric porphyrin reagent because the lead ions became complexed by EDTA.

TABLE 6

| µg/dL $Pb^{2+}$ | | |
|---|---|---|
| added | found | $\Delta A_{463}$ |
| 0.0 | 0.0 | 0.0000 |
| 200.0 | 2.1 | 0.0013 |

B. This example details the analysis of EDTA treated whole blood pretreated according to the procedure of Example 4 with the 10% (w/v) trichloroacetic acid, 0.5M $NaNO_3$ and 0.1M $Ca(NO_3)_2$ releasing reagent of Example 2c. The absorbance data in Table 7 were obtained in accordance with Example 6A. The absorbance data in Table 8 were obtained in accordance with Example 6B.

TABLE 7

| µg/dL $Pb^{2+}$ | $\Delta A_{463}$ (std) |
|---|---|
| 0.0 | 0.0000 |
| 5.0 | 0.0072 |
| 10.0 | 0.0143 |
| 20.0 | 0.0275 |
| 40.0 | 0.0547 |

TABLE 8

| μg/dL Pb²⁺ | | |
|---|---|---|
| added | found | ΔA₄₆₃ (sample) |
| 0.0 | 0.0 | 0.0000 |
| 10.0 | 8.7 | 0.0060 |
| 20.0 | 18.1 | 0.0125 |
| 35.0 | 36.6 | 0.0240 |
| 50.0 | 52.2 | 0.0350 |
| 75.0 | 76.8 | 0.0570 |
| 100.0 | 98.5 | 0.0670 |

The concentration of lead ions in the supernatant liquids were calculated from $\Delta A_{463}$(standard) data in Table 7, and $\Delta A_{463}$(sample) data in Table 8 according to the following equation:

$$\mu g/dL\ Pb^{2+}(found) = A_{463}(sample)/A_{463}(std) \times 2 \times \mu g/dL\ Pb^{2+}(std)\ \ [II]$$

The results in Table 8 indicate that the addition of calcium ions to the releasing agent promoted the release of lead ions from EDTA anticoagulated whole blood by blocking binding sites in the EDTA that would complex with lead ions.

EXAMPLE 9

Analysis of Lead Controls and Reference Materials

A. Lyophilized human whole blood obtained from Utak Laboratories in Valencia, Calif. was pretreated in accordance with the procedure of Example 4 with the 10% trichloroacetic acid/0.5M NaNO₃/0.1M Ca(NO₃)₂ releasing reagent of Example 2c. It was not known which anticoagulant was present in the lyophilized whole blood. Under these conditions, where the anticoagulant was unknown, the releasing reagent of example 2c was found to have universal application, regardless of the nature of the whole blood anticoagulant. The supernatants were assayed according to the procedure of Example 6B.

TABLE 9

| (μg/dL Pb²⁺) | found | ΔA₄₆₃ |
|---|---|---|
| Level I (8–16) | 9.1 | 0.0060 |
| Level II (21–29) | 20.5 | 0.0144 |
| Level III (32–40) | 29.8 | 0.0207 |
| Level IV (51–63) | 49.4 | 0.0340 |

The concentration of lead ions detailed in Table 9 were calculated in accordance with equation II shown in Example 8B.

B. Analysis of National Institute of Standards (NIST) Reference Materials

The NIST reference materials constitute bovine whole blood anticoagulated with EDTA. The NIST bovine blood was pretreated according to the procedure of Example 4 with 10% trichloroacetic acid/0.5M NaNO₃/0.1M Ca(NO₃)₂ releasing reagent of Example 2c. The supernatants were assayed according to the procedure of Example 6B, with the data as follows:

TABLE 10

| (μg/dL Pb²⁺) | found | ΔA₄₆₃ |
|---|---|---|
| 955a-1* (5.01) | 3.7 | 0.003 |
| 955a-2* (13.53) | 14.0 | 0.010 |
| 955a-3* (30.63) | 28.7 | 0.020 |
| 955a-4* (54.40) | 58.2 | 0.040 |

*NIST control numbers

The extraction of lead ions from NIST reference materials was confirmed by the spectral lead response of the colorimetric porphyrin reagent of Example 1b in contact with NIST supernatants shown in FIG. 3. The spectrum was recorded by scanning the assay mixture obtained according to the procedure of Example 6B from 700 to 300 nm on a Cary-3 spectrophotometer.

The results from Examples 8B, 9A and 9B demonstrate that the working formulation of the releasing reagent extracts lead ions quantitatively from a variety of matrices.

The present invention provides a universal releasing reagent for extracting lead ions from a variety of biological matrices such as serum, urine, milk, and the like. The releasing reagent is especially useful in extracting lead ions from human whole blood anticoagulated with either heparin or EDTA, and bovine EDTA whole blood, or wherein the nature of the anticoagulant is unknown, as often occurs with lyophilized human whole blood.

What is claimed is:

1. A method for releasing the lead ion content from a biological matrix, comprising contacting the biological matrix with a lead ion releasing reagent comprising a solution of sufficient amounts of an acid capable of releasing lead ions from said biological matrix, and sufficient amounts of a substance capable of solubilizing the released lead ions, to thereby form a supernatant solution containing the released lead ions, and a precipitate comprising the residue of the biological matrix, wherein said solubilizing substance is an alkali metal salt having an anion selected from the group consisting of nitrate, chloride, and bromide.

2. The method of claim 1, wherein the acid is selected from the group consisting of trichloroacetic acid, perchloric acid, and 5-sulfosalicylic acid.

3. The method of claim 2, wherein the acid is trichloroacetic acid.

4. The method of claim 1, wherein the acid is present in a concentration of about 5% (w/v) to about 25% (w/v).

5. The method of claim 1, wherein the alkali metal is selected from the group consisting of sodium, potassium and lithium.

6. The method of claim 1, wherein the alkali metal salt is sodium nitrate.

7. The method of claim 1, wherein the alkali metal salt has a concentration of about 0.1M to about 1.0M.

8. The method of claim 1, wherein the biological matrix is whole blood anticoagulated with heparin.

9. The method of claim 1, wherein the biological matrix is whole blood anticoagulated with EDTA.

10. The method of claim 1, wherein the lead ion releasing reagent also includes sufficient amounts of a substance capable of preventing the released lead ions from forming a complex with the EDTA anticoagulant.

11. The method of claim 10, wherein the substance capable of preventing the released lead ions from forming a complex with the EDTA anticoagulant is derived from an alkaline earth metal salt having an anion selected from the group consisting of nitrate, chloride and bromide.

12. The method of claim 11, wherein the alkaline earth metal salt is calcium nitrate.

13. The method of claim 11, wherein the alkaline earth metal salt has a concentration of about 0.04M to about 1.0M.

14. The method of claim 1, wherein the biological matrix is lyophilized whole blood.

15. The method of claim 1, wherein the biological matrix is selected from the group consisting of whole blood, serum, urine, and milk.

16. The method of claim 1, wherein the supernatant solution is separated from the precipitate by means selected from the group consisting of centrifugation and filtration.

17. A reagent for releasing the lead ion content from a biological matrix comprising a solution of sufficient amounts of an acid capable of releasing lead ions from said biological matrix, and sufficient amounts of a substance capable of solubilizing the released lead ions, to thereby form a supernatant solution containing the released lead ions, and a precipitate comprising the residue of the biological matrix, wherein said solubilizing substance is an alkali metal salt having an anion selected from the group consisting of nitrate, chloride, and bromide.

18. The reagent of claim 17, wherein the acid is present in a concentration of about 5% (w/v) to about 25% (w/v).

19. The reagent of claim 17, wherein the acid is selected from the group consisting of trichloroacetic acid, perchloric acid, and 5-sulfosalicylic acid.

20. The reagent of claim 19, wherein the acid is trichloroacetic acid.

21. The reagent of claim 17, wherein the alkali metal salt has a concentration of about 0.1M to about 1.0M.

22. The reagent of claim 17, wherein the alkali metal is selected from the group consisting of sodium, potassium and lithium.

23. The reagent of claim 17, wherein the, alkali metal salt is sodium nitrate.

24. The reagent of claim 17, wherein the biological matrix is whole blood anticoagulated with heparin.

25. The reagent of claim 17, wherein the biological matrix is whole blood anticoagulated with EDTA.

26. The reagent of claim 17, wherein the lead ion releasing reagent also includes sufficient amounts of a substance capable of preventing the released lead ions from forming a complex with the EDTA anticoagulant.

27. The reagent of claim 17, wherein the substance capable of preventing the released lead ions from forming a complex with the EDTA anticoagulant is derived from an alkaline earth metal salt having an anion selected from the group consisting of nitrate, chloride and bromide.

28. The reagent of claim 27, wherein the alkaline earth metal salt has a concentration of about 0.04M to about 1.0M.

29. The reagent of claim 27, wherein the alkaline earth metal salt is calcium nitrate.

30. The reagent of claim 17, wherein the biological matrix is lyophilized whole blood.

31. The reagent of claim 17, herein the biological matrix is selected from the group consisting of whole blood, serum, urine, and milk.

32. The reagent of claim 17, wherein the supernatant solution is separated from the precipitate by means selected from the group consisting of centrifugation and filtration.

33. A method for determining the amount of lead ions in whole blood anticoagulated with heparin, comprising:
a) contacting the whole blood with a lead ion releasing reagent comprising a solution of sufficient amounts of an acid capable of releasing ions from said whole blood, and sufficient amounts of a substance capable of solubilizing the released lead ions, to thereby form a supernatant solution containing the released lead ions, and a residue comprising the precipitated whole blood protein content, wherein said solubilizing substance is an alkali metal salt having an anion selected from the group consisting of nitrate, chloride, and bromide;
b) separating the supernatant solution from the precipitate; and
c) measuring the lead ion content in the supernatant solution.

34. The method of claim 33, wherein the supernatant solution is separated from the precipitate by means selected from the group consisting of centrifugation and filtration.

35. The method of claim 33, wherein the lead ion content is measured by means selected from the group consisting of atomic absorption, anodic stripping voltametry, spectrophotometric analysis, and enzyme based biodetection systems.

36. The method of claim 33, wherein the lead ion content in the supernatant solution is measured by means of spectrophotometric analysis.

37. The method of claim 36, wherein a colorimetric porphyrin based reagent is used in the spectrophotometric analysis.

38. The method of claim 33, wherein the acid is selected from the group consisting of trichloroacetic acid, perchloric acid, and 5-sulfosalicylic acid.

39. The method of claim 38, wherein the acid is trichloroacetic acid.

40. The method of claim 33, wherein the acid is present in a concentration of about 5% (w/v) to about 25% (w/v).

41. The method of claim 33, wherein the alkali metal is selected from the group consisting of sodium, potassium and lithium.

42. The method of claim 41, wherein the alkali metal salt is sodium nitrate.

43. The method of claim 33, wherein the alkali metal salt has a concentration of about 0.1M to about 1.0M.

44. A method for determining the amount of lead ions in whole blood anticoagulated with EDTA, comprising:
a) contacting the whole blood with a lead ion releasing reagent comprising a solution of sufficient amounts of an acid capable of releasing lead ions from said whole blood, and sufficient amounts of a first substance capable of solubilizing the released lead ions, and a second substance capable of preventing the EDTA from forming a complex with the lead ions, to thereby form a supernatant solution containing the released lead ions, and a precipitate comprising the whole blood protein content, wherein said solubilizing substance is an alkali metal salt having an anion selected from the group consisting of nitrate chloride, and bromide;
b) separating the supernatant solution from the precipitate; and
c) measuring the lead ion content in the supernatant solution.

45. The method of claim 44, wherein the supernatant solution is separated from the precipitate by means selected from the group consisting of centrifugation and filtration.

46. The method of claim 44, wherein the lead ion content is measured by means selected from the group consisting of atomic absorption, anodic stripping voltametry, spectrophotometric analysis, and enzyme based biodetection systems.

47. The method of claim 44, wherein the lead ion content in the supernatant solution is measured by means of spectrophotometric analysis.

48. The method of claim 47, wherein a calorimetric porphyrin based reagent is used in the spectrophotometric analysis.

49. The method of claim 44, wherein the acid is selected from the group consisting of trichloroacetic acid, perchloric acid, and 5-sulfosalicylic acid.

50. The method of claim 49, wherein the acid is trichloroacetic acid.

51. The method of claim 44, wherein the acid is present in a concentration of about 5% (w/v) to about 25% (w/v).

52. The method of claim 44, wherein the alkali metal is selected from the group consisting of sodium, potassium and lithium.

53. The method of claim 52, wherein the alkali metal salt is sodium nitrate.

54. The method of claim 44, wherein the alkali metal salt has a concentration of about 0.1M to about 1.0M.

55. The method of claim 44, wherein the substance capable of preventing the released lead ions from forming a complex with the EDTA anticoagulant is derived from an alkaline earth metal salt having an anion selected from the group consisting of nitrate, chloride and bromide.

56. The method of claim 55, wherein the alkaline earth metal salt is calcium nitrate.

57. The method of claim 55, wherein the alkaline earth metal salt has a concentration of about 0.04M to about 1.0M.

58. A method for determining the amount of lead ions in whole blood having an unknown anticoagulant, comprising:
   a) contacting the whole blood with a lead ion releasing reagent comprising a solution of sufficient amounts of an acid capable of releasing lead ions from said whole blood, and sufficient amounts of a first substance capable of solubilizing the released lead ions, and sufficient amounts of a second substance capable of preventing the released lead ions from forming a complex with any EDTA that is present, to thereby form a supernatant solution containing the released lead ions, and a precipitate comprising the whole blood protein content, wherein said solubilizing substance is an alkali metal salt having an anion selected from the group consisting of nitrate, chloride, and bromide;
   b) separating the supernatant solution from the precipitate; and
   c) measuring the lead ion content in the supernatant solution.

59. The method of claim 58, wherein the supernatant solution is separated from the precipitate by means selected from the group consisting of centrifugation and filtration.

60. The method of claim 58, wherein the lead ion content is measured by means selected from the group consisting of atomic absorption, anodic stripping voltametry, spectrophotometric analysis, and enzyme based biodetection systems.

61. The method of claim 58, wherein the lead ion content in the supernatant solution is measured by means of spectrophotometric analysis.

62. The method of claim 61, wherein a colorimetric porphyrin based reagent is used in the spectrophotometric analysis.

63. The method of claim 58, wherein the acid is selected from the group consisting of trichloroacetic acid, perchloric acid, and 5-sulfosallcylic acid.

64. The method of claim 63, wherein the acid is trichloroacetic acid.

65. The method of claim 58, wherein the acid is present in a concentration of about 5% (w/v) to about 25% (w/v).

66. The method of claim 58, wherein the alkali metal is selected from the group consisting of sodium, potassium and lithium.

67. The method of claim 66, wherein the alkali metal salt is sodium nitrate.

68. The method of claim 58, wherein the alkali metal salt has a concentration of about 0.1M to about 1.0M.

69. The method of claim 58, wherein the substance capable of preventing the released lead ions from forming a complex with the EDTA anticoagulant is derived from an alkaline earth metal salt having an anion selected from the group consisting of nitrate, chloride and bromide.

70. The method of claim 69, wherein the alkaline earth metal salt is calcium nitrate.

71. The method of claim 69, wherein the alkaline earth metal salt has a concentration of about 0.04M to about 1.0M.

* * * * *

UNITED STATES PATENT AND TRADEMARK OFFICE
CERTIFICATE OF CORRECTION

PATENT NO : 5,891,736
DATED : April 6, 1999
INVENTOR(S): Eddy CHAPOTEAU et al

It is certified that error appears in the above-identified patent and that said Letters Patent is hereby corrected as shown below:

Table 5 at column 7, lines 55-65 replaces Table 4, at column 8, lines 9 to 14.

Table 4 at column 8, lines 9-14 replaces Table 5, at column 7, lines 55, to 65.

In Claim 10 at column 10, line 57, change "claim 1" to --claim 9--.

In Claim 31 at column 11, line 54, change "herein" to --wherein--.

In Claim 48 at column 12, line 65, change "calorimetric" to --colorimetric--.

In Claim 63 at column 14, line 18, change "5-sulfosallcylic" to

--5-sulfosalicylic--.

Signed and Sealed this

Fifth Day of October, 1999

Attest:

Q. TODD DICKINSON

*Attesting Officer*    *Acting Commissioner of Patents and Trademarks*